(12) United States Patent
Meyerhoff et al.

(10) Patent No.: US 7,622,075 B2
(45) Date of Patent: Nov. 24, 2009

(54) FILMS FOR DETECTING FLUORIDE

(75) Inventors: Mark E. Meyerhoff, Ann Arbor, MI (US); Ibrahim H. A. Badr, Cairo (EG)

(73) Assignee: The Regents of The University of Michigan, Ann Arbor, MI (US)

( * ) Notice: Subject to any disclaimer, the term of this patent is extended or adjusted under 35 U.S.C. 154(b) by 557 days.

(21) Appl. No.: 11/330,509

(22) Filed: Jan. 12, 2006

(65) Prior Publication Data

US 2006/0216194 A1    Sep. 28, 2006

Related U.S. Application Data

(60) Provisional application No. 60/664,310, filed on Mar. 22, 2005.

(51) Int. Cl.
*G01N 31/22* (2006.01)
*G01N 21/76* (2006.01)
*C12Q 1/68* (2006.01)
*G01N 17/00* (2006.01)
*B32B 15/00* (2006.01)

(52) U.S. Cl. .................... 422/56; 422/50; 422/52; 422/57; 422/91; 428/432

(58) Field of Classification Search ............... 422/50, 422/52, 56, 57, 91; 428/432
See application file for complete search history.

(56) References Cited

U.S. PATENT DOCUMENTS

| 6,472,073 | B1 | 10/2002 | Singh et al. | |
|---|---|---|---|---|
| 2003/0162960 | A1* | 8/2003 | Sessler et al. | ............... 540/145 |
| 2004/0018631 | A1 | 1/2004 | Ward et al. | |

FOREIGN PATENT DOCUMENTS

GB    2243917    * 11/1991

OTHER PUBLICATIONS

Antonisse, M. M. G., B. H. M. Snellink-Ruël, A. C. Ion, J. F. J. Engbersen, D. N. Reinhoudt, "Synthesis of Novel Uranyl Salophene Derivatives and Evaluation as Sensing Molecules in Chemically Modified Field Effect Transistors (CHEMFETs)," J Chem. Soc. Perkin Trans. 2, 1999, pp. 1211-1281.

(Continued)

*Primary Examiner*—Jill Warden
*Assistant Examiner*—Dean Kwak
(74) *Attorney, Agent, or Firm*—Dierker & Associates, P.C.

(57) ABSTRACT

A film for detecting fluoride concentrations is disclosed. The film includes an organic matrix having a lipophilic aluminum compound incorporated therein. The lipophilic aluminum compound is adapted to selectively bind with fluoride ions via a binding interaction. The fluoride is detectable through optical or electrochemical detection of the binding interaction.

24 Claims, 6 Drawing Sheets

OTHER PUBLICATIONS

ASTM International; "Standard Test Methods for Fluoride Ion in Water;" D1179-04; ASTM: West Conshohocken, PA, 2005, pp. 1-6.

Bergman, I., "Rapid-response Atmospheric Oxygen Monitor Based on Fluorescence Quenching," Nature 1968, 218, p. 396.

Harwood, J. E., "The Use of an Ion-Selective Electrode for Routine Fluoride Analyses on Water Samples," Water Research 1969, 3, pp. 273-280.

Kaizu, Y., N. Misu, K. Tsuji, Y. Kaneko, H. Kobayashi, "Electronic Spectra of the Aluminum(III) Complexes of 5,10,15,-20-Tetraphenylporphin and 2,3,7,8,12,13,17,18-Octaethylporphin," Bull. Chem. Soc. Jpn. 1985, 58, 103-108.

Lindner, E., K. Tóth, J. Jeney, M. Horváth, E. Pungor, I. Bitter, B. Ágai, L. Töke, "Novel Bis(Crown Ether)-Based Potassium Sensor for Biological Applications," Mikrochimica Acta 1990, 1, pp. 157-168.

Pioda, L. A. R., V. Stankova, W. Simon, "Highly Selective Potassium Ion Responsive Liquid-Membrane Electrode," Anal. Lett. 1969, 2, pp. 665-674.

Schulthess, P., D. Ammann, W. Simon, C. Caderas, R. Stepánek, B. Kräeutler, "116. Lipophilic Derivative of Vitamin $B_{12}$ as a Selective Carrier for Anions," Helv. Chim. Acta, 1984, 67, pp. 1026-1032.

Yamamoto, H., Shinkai, S., "Molecular Design of Calix[4]arene-Based Sodium-Selective Electrodes Which Show Remarkably High $10^{5.0}$-$10^{5.3}$ Sodium/Potassium Selectivity," Chem. Lett. 1994, 6, pp. 1115-1118.

Downs, A. J., (Ed.) Chemistry of Aluminum, Gallium, Indium and Thallium, Coordination and Solution of Chemistry, Chapman & Hall: Glasgow, 1993, pp. 432-449.

Kunz, W., J. Henle, W. W. Ninham, "'Zur Lehre von der Wirkung der Salze' (about the science of the effect of salts): Franz Hofmeister's historical papers," Elsevier, Current Opinion in Colloid and Interface Science, 2004, pp. 1-19.

Hulanicki, A., R. Lewandowski, "Some Properties of Ion-Selective Electrodes Based on Poly(Vinyl Chloride) Membranes with Liquid-Ion-Exchanger," Chem. Anal. Warsaw 1974, 19, 53-61.

Kotrly, S., Sucha, L., Handbook of Chemical Equilibria in Analytical Chemistry, Stability Constants of Complexes with Inorganic Ligands, John Wiley & Sons: New York, 1985, pp. 132-135.

Landis, W. G., J. J. DeFrank, "Enzymatic Hydrolysis of Toxic Organofluorophosphate Compounds," Methods and Applications in Biodegradation, Biotechnology Series 1990, vol. 4 (Biotechnol. Biodegrad.), pp. 183-201.

Smith, R. M., Martell, A. E., Critical Stability Constants; vol. 4: Inorganic Complexes, Plenum: New York, 1974, pp. 96-103.

International Search Report for S.N. PCT/US2006/07330 dated Aug. 8, 2007 (3 pages).

Adler, A. D., F. R. Longo, J. D. Finarelli, J. Goldmacher, J. Assour, L. Korsakoff, "A Simplified Synthesis for meso-Tetraphenylporphin," J. Org. Chem. 1967, 32, p. 476.

Aida, T., S. Inoue, "Activation of Carbon Dioxide with Aluminum Porphyrin and Reaction with Epoxide. Studies on (Tetraphenylporphinato)aluminium Alkoxide Having a Long Oxyalkylene Chain as the Alkoxide Group," J. Am. Chem. Soc. 1983,105, pp. 1304-1309.

Aida T., K. Wada, S. Inoue, "Copolymerization of Epoxides by Aluminium Porphyrin. Reactivity of (Porphinato)aluminum Alkoxide as Growing Species," Macromolecules 1987, 20, pp. 237-241.

Antonisse, M. M. G., D. N. Reinhoudt, "Potentiometric Anion Selective Sensors," Electroanalysis 1999, 11, pp. 1035-1048.

Aoba, T., O. Fejerskov, "Dental Fluorosis: Chemistry and Biology," Crit. Rev. Oral Biol. Med. 2002, 13, pp. 155-170.

Arndt, P., A. Spannenberg, W. Baumann, V. V. Burlakov, U. Rosenthal, S. Becke, T. Weiss, "Reactions of Zicronocene 2-Vinylpyridine Complexes with Diisobutylaluminum Hydride and Fluoride," Organometallics 2004, 23, pp. 4792-4795.

Aylott, J. W., "Optical Nanosensors—An Enabling Technology for Intracellular Measurements," Analyst 2003, 128, pp. 309-312.

Badr, I. H. A., M. Diaz, M. F. Hawthorne, L. G. Bachas, "Mercuracarborand "Anti-Crown Ether"-Based Chloride-Sensitive Liquid/Polymeric Membrane Electrodes," Anal. Chem. 1999, 71, pp. 1371-1377.

Badr, I. H. A., M. E. Meyerhoff, "Fluoride-Selective Optical Sensor Based on Aluminum(III)-Octaethylporphyrin in Thin Polymeric Film: Further Characterization and Practical Application," Anal. Chem. 2005, 77, pp. 6719-6728.

Badr, I. H. A., M. E. Meyerhoff, "Highly Selective Optical Fluoride Ion Sensor with Submicromolar Detection Limit Based on Aluminum(III) Octaethylporphyrin in Thin Polymeric Film," J. Am. Chem. Soc. 2005, 127, pp. 5318-5319.

Badr, I. H. A., M. E. Meyerhoff, "Highly Selective Single-Use Fluoride Ion Optical Sensor Based on Aluminium(III)-Salen Complex in Thin Polymeric Film," Anal. Chim. Acta 2005, 553, pp. 169-176.

Badr, I. H. A., R. D. Johnson, M. Diaz, M. F. Hawthorne, L. G. Bachas, "A Selective Optical Sensor Based on [9]Mercuracarborand-3, a New Type of Ionophore with a Chloride Complexing Cavity," Anal. Chem. 2000, 72, pp. 4249-4254.

Bakker, E., M. E. Meyerhoff, "Ion-Selective Electrodes for Measurements in Biological Fluids," Encyclopedia of Electrochemistry 2002, 9, pp. 277-307.

Bakker, E., R. K. Meruva, E. Pretsch, M. E. Meyerhoff, "Selectivity of Polymer Membrane-Based Ion-Selective Electrodes: Self-Consistent Model Describing the Potentiometric Response in Mixed Ion Solutions of Different Charge," Anal. Chem. 1994, 66, pp. 3021-3030.

Bakker, E., E. Malinowska, R. D. Schiller, M. E. Meyerhoff, "Anion-Selective Membrane Electrodes Based on Metalloporphyrins: The Influence of Lipophilic Anionic and Cationic Sites on Potentiometric Selectivity," Talanta 1994, 41, pp. 881-890.

Bakker, E., E. Pretsch, P. Bühlmann, "Selectivity of Potentiometric Ion Sensors," Anal. Chem. 2000, 72, pp. 1127-1133.

Bakker, E., P. Bühlmann, E. Pretsch, "Carrier-Based Ion-Selective Electrodes and Bulk Optodes. 1. General Characteristics," Chem. Rev. 1997, 97, 3083-3132.

Becker, C., I. Kieltsch, D. Broggini, A. Mezzetti, "Bridging Fluorides and Hard/Soft Mismatch in $d^6$ and $d^8$ Complexes: The Case of $[Tl(\mu$-$F)_3Ru(PPh_3)_3]$," Inorg. Chem. 2003, 42, pp. 8417-8429.

Bühlmann, P., E. Pretsch, E. Bakker, "Carrier-Based Ion-Selective Electrodes and Bulk Optodes. 2. Ionophores for Potentiometric and Optical Sensors," Chem. Rev. 1998, 98, pp. 1593-1687.

Chaniotakis, N. A., S. B. Park, M. E. Meyerhoff, "Salicylate-Selective Membrane Electrode Based on Tin(IV) Tetraphenylporphyrin," Anal. Chem. 1989, 61, pp. 566-570.

Chaniotakis, N. A., A. M. Chasser, M. E. Meyerhoff, J. T. Groves, "Influence of Porphyrin Structure on Anion Selectivities of Manganese(III) Porphyrin Based Membrane Electrodes," Anal. Chem. 1988, 60, pp. 185-188.

Chen, X., C.-G. Zhan, "Theoretical Determination of Activation Free Energies for Alkaline Hydolysis of Cyclic and Acyclic Phosphodiesters in Aqueous Solution," J. Phys. Chem. A 2004, 108, 6407-6413.

Dai, S., Q. Ye, E. Wang, M. E. Meyerhoff, "Optical Detection of Polycations via Polymer Film-Modified Microtiter Plates: Response Mechanism and Bioanalytical Applications," Anal. Chem. 2000, 72, pp. 3142-3149.

Eugster, R., T. Rosatzin, B. Rusterholz, B. Aebersold, U. Pedrazza, D. Rüegg, A. Schmid, U. E. Spichiger, W. Simon, "Plasticizers for Liquid Polymeric Membranes of Ion-Selective Chemical Sensors," Anal. Chim. Acta 1994, 289, pp. 1-13.

Frant, M. S., J. W. Ross, "Electrode for Sensing Fluoride Ion Activity in Solution," Science 1966, 154, pp. 1553-1555.

Fu, B., E. Bakker, J. H. Yun, V. C. Yang, M. E. Meyerhoff, "Response Mechanism of Polymer Membrane-Based Potentiometric Polyion Sensors," Anal. Chem. 1994, 66, pp. 2250-2259.

Fukushima, K., K. Funatsu, A. Ichimura, Y. Sasaki, M. Suzuki, T. Fujihara, K. Tsuge, T. Imamura, "Synthesis and Properties of Rhodium(III) Porphyrin Cyclic Tetramer and Cofacial Dimer," Inorg. Chem. 2003, 42, pp. 3187-3193.

Ganjali, M. R., M. Rezapour, M. R. Pourjavid, M. Salavati-Niasari, "Highly Selective PVC-Membrane Electrodes Based on Co(II)-Salen for Determination of Nitrite Ion," Anal. Sci. 2003, 19, pp. 1127-1131.

Górski, Ł., M. E. Meyerhoff, E. Malinowska, "Polymeric Membrane Electrodes with Enhanced Fluoride Selectivity Using Zr(IV)-Porphyrins Functioning as Neutral Carriers," Talanta 2004, 63, pp. 101-107.

Górski, Ł., E. Malinowska, "Fluoride-Selective Sensors Based on Polyurethane Membranes Doped with Zr(IV)-Porphyrins," Anal. Chim. Acta 2005, 540, pp. 159-165.

Górski, Ł., E. Malinowska, P. Parzuchowski, W. Zhang, M. E. Meyerhoff, "Recognition of Anions Using Metalloporphyrin-Based Ion-Selective Membranes: State-of-the-Art," Electroanal 2003, 15, pp. 1229-1235.

Grushin, V. V., W. J. Marshall, "The Fluoro Analogue of Wilkinson's Catalyst and Unexpected Ph-Cl Activiation," J. Am. Chem. Soc. 2004, 126, pp. 3068-3069.

Guilard, R., A. Zrineh, A. Tabard, A. Endo, B. C. Han, C., Lecomte, M. Souhassou, A. Habbou, M. Ferhat, K. M. Kadish, "Synthesis and Spectroscopic and Electrochemical Characterization of Ionic and α-Bonded Aluminum(III) Porphyrins. Crystal Structure of Methyl(2,3,7,8,12,13,17,18-octaethylporphinato)aluminum(III), (OEP)Al(CH$_3$)," Inorg. Chem. 1990, 29, pp. 4476-4482.

Hattori, H., M. Hoshino, T. Wakii, A. Yuchi, "Effects of Two-Phase Reactions on Composition and Potential Response of Zirconium(IV)-Tetraphenylporphyrin Complexes as Carrier for Citrate-Selective Electrode," Anal. Chem. 2004, 76, pp. 5056-5062.

Hungerford, G., M. R. Pereira, J. A. Ferreira, T. M. R. Viseu, A. F. Coelho, M. Isabel, C. Ferreira, K. Suhling, "Probing Si and Ti Based Sol-Gel Matrices by Fluorescence Techniques," J. Fluores 2002, 12, pp. 397-417.

Hurtado, R., J. Gardea-Torresde, "Environmental Evaluation of Fluoride in Drinking Water at "Los Altos De Jalisco," in the Central Mexico Region," J. Toxicol. Environ. Health 2004, A 67, pp. 1741-1753.

Hutchins, R. S., P. Molina, M. Alajarin, A. Vidal, L. G. Bachas, "Use of a Guanidinium Ionophore in a Hydrogen Sulfite-Selective Electrode," Anal. Chem. 1994, 66, pp. 3188-3192.

Johnson, R. D., L. G. Bachas, "Ionophore-Based Ion-Selective Potentiometric and Optical Sensors," Anal. Bioanal. Chem. 2003, 376, pp. 328-341.

Jones, C. M., H. Worthington, "Water Fluoridation, Poverty and Tooth Decay in 12-Year-Old Children," J. dent. 2000, 28, pp. 389-393.

Kamata, S., K. Onoyama, "Lead-Selective Membrane Electrode Using Methylene Bis(diisobutyldithiocarbamate) Neutral Carrier," Anal. Chem. 1991, 63, pp. 1295-1298.

Kibbey, C. E., S. B. Park, G. DeAdwyler, M. E. Meyerhoff, "Further Studies on the Potentiometric Salicylate Response of Polymeric Membranes Doped with Tin(IV)-Tetraphenylporphyrins," J. Electroanal. Chem. 1992, 335, pp. 135-149.

Komatsu, T., T. Yanagimoto, Y. Furubayashi, J. Wu, E. Tsuchida, "Self-Assembled Fibers Made of Lipidporphyrinato-Zinc(II) and—Iron(II) Complexes with an Intramolecular Coordinated Axial Imidazole," Langmuir 1999, 15, pp. 4427-4433.

Kuswandi, B., R. Andres, R. Narayanaswamy, "Optical Fibre Biosensors Based on Immobilised Enzymes," Analyst 2001, 126, pp. 1469-1491.

Lerchi, M., E. Reitter, W. Simon, E. Pretsch, D. A. Chowdhury, S. Kamata, "Bulk Optodes Based on Neutral Dithiocarbamate Ionophores with High Selectivity and Sensitivity for Silver and Mercury Cations," Anal. Chem. 1994, 66, pp. 1713-1717.

Liu, J., Y. Masuda, E. Sekido, "Response Properties of an Ion-Selective Polymeric Membrane Phosphate Electrode Prepared with Cobalt Phthalocyanine and Characterization of the Electrode Process," J. Electroanal. Chem. 1990, 291, pp. 67-79.

Li, Z.-Q., Z.-Y. Wu, R. Yuan, M. Ying, G.-L. Shen, R.-Q. Yu, "Thiocyanate-Selective PVC Membrane Electrodes Based on Mn(II) Complex of N,N'-Bis-(4-Phenylazosalicylidene) α-Phenylene Diamine as a Neutral Carrier," Electrochim. Acta 1999, 44, pp. 2543-2548.

Malinowska, E., Ł. Górski, M. E. Meyerhoff, "Zirconium(IV)-Porphyrins as Novel Ionophores for Fluoride-Selective Polymeric Membrane Electrodes," Anal. Chim. Acta 2002, 468, pp. 133-141.

Malinowska, E., M. E. Meyerhoff, "Role of Axial Ligation on Potentiometric Response of Co(III) Tetraphenylporphyrin-Doped Polymeric Membranes to Nitrite Ions," Anal. Chim. Acta 1995, 300, pp. 33-43.

Malinowska, E., J. Niedziółka, M. E. Meyerhoff, "Potentiometric and Spectroscopic Characterization of Anion Selective Electrodes Based on Metal(III) Porphyrin Ionophores in Polyurethane Membranes," Anal. Chim. Acta 2001, 432, pp. 67-78.

Mitchell-Koch, J. T., E. Malinowska, M. E. Meyerhoff, "Gallium(III)-Schiff Base Complexes as Novel Ionophores for Fluoride Selective Polymeric Membrane Electrodes," Electroanalysis 2005, 17, pp. 1347-1353.

Morf, W. E., K. Seiler, B. Rusterholz, W. Simon, "Design of a Calcium-Selective Optode Membrane Based on Neutral Ionophores," Anal. Chem. 1990, 62, pp. 738-742.

Narayanaswamy, R., D. A. Russell, F. Sevilla, "Optical-Fibre Sensing of Fluoride Ions in a Flow-Stream," Talanta 1988, 35, pp. 83-88.

Oesch, U., D. Ammann, H. V. Pham, U. Wuthier, R. Zünd, W. Simon, "Design of Anion-Selective Membranes for Clinically Relevant Sensors," J. Chem. Soc. Faraday Trans. 1, 1986, 82, pp. 1179-1186.

Oggenfuss, P., W. E. Morf, U. Oesch, D. Ammann, E. Pretsch, W. Simon, "Neutral-Carrier-Based Ion-Selective Electrodes," Anal. Chim. Acta 1986, 180, pp. 299-311.

Oldham, P. B., M. E. McCarroll, L. B. McGown, I. M. Warner, "Molecular Fluorescence, Phosphorescence, and Chemiluminescence Spectrometry," Anal. Chem. 2000, 72, pp. 197-209.

Panunzio, M., K. Rossi, E. Tamanini, E. Campana, G. Martelli, "Synthesis of Enantiomerically Pure (S)- and (R)-Fluoxetine (Prozac®) via a Hetero Diels-Alder Strategy," Tetrahedron Asymmetry 2004, 15, pp. 3489-3493.

Parzuchowski, P. G., J. W. Kampf, E. Roźniecka, Y. Kondratenko, E. Malinowska, M. E. Meyerhoff, "Gallium(III) and Indium(III) Octaethylporphyrin Dimeric Complexes with a Single μ-Hydroxo Bridge: Synthesis, Structure and Stability in Anion-Containing Organic Media," Inorg. Chim. Acta 2003, 355, pp. 302-313.

Perdikaki, K., I. Tsagkatakis, N. A. Chaniotakis, R. Altmann, K. Jurkschat, G. Reeske, "Selective Fluoride Recognition and Potentiometric Properties of Ion-Selective Electrodes Based on Bis(halodiphenylstannyl)alkanes," Anal. Chim. Acta 2002, 467, pp. 197-204.

Qin, Y., E. Bakker, "Elimination of Dimer Formation in In$^{III}$Porphyrin-Based Anion-Selective Membranes by Covalent Attachment of the Ionophore," Anal. Chem. 2004, 76, pp. 4379-4386.

Qin, W., P. Parzuchowski, W. Zhang, M. E. Meyerhoff, "Optical Sensor for Amine Vapors Based on Dimer-Monomer Equilibrium of Indium(III) Octaethylporphyrin in a Polymeric Film," Anal. Chem. 2003, 75, 332-340.

Rakita, P. E., "Dentrifice Fluoride," J. Chem. Ed. 2004, 81, pp. 677-680.

Rum, G., W.-Y. Lee, J. Gardea-Torresdey, "Applications of a U.S. EPA-Approved Method for Fluoride Determination in an Environmental Chemistry Laboratory: Fluoride Detection in Drinking Water," J. Chem. Ed. 2000, 77, pp. 1604-1606.

Russell, D. A., R. Narayanaswamy, "Fibre Optic Fluorimetric Determination of Fluoride Ions," Analyst 1989, 114, pp. 381-385.

Seiler, K., W. Simon, "Theoretical Aspects of Bulk Optode Membranes," Anal. Chim. Acta 1992, 266, pp. 73-87.

Shahrokhian, S., M. K. Amini, R. Kia, S. Tangestaninejad, "Salicylate-Selective Electrodes Based on Al(III) and Sn(IV) Salophens," Anal. Chem. 2000, 72, pp. 956-962.

Shahrokhian, S., A. Hamzehloei, M. Bagherzadeh, "Chromium(III) Porphyrin as a Selective Ionophore in a Salicylate-Selective Membrane Electrode," Anal. Chem. 2002, 74, pp. 3312-3320.

Shamsipur, M., M. Javanbakht, A. R. Hassaninejad, H. Sharghi, M. R. Ganjali, M. F. Mousavi, "Highly Selective PVC-Membrane Electrodes on Three Derivatives of (Tetraphenylporphyrinato)Cobalt(III) Acetate for Determination of Trace Amounts of Nitrate Ion," Electroanalysis 2003, 15, pp. 1251-1259.

Simonian, A. L., J. K. Grimsley, A. W. Flounders, J. S. Schoeniger, T.-C. Cheng, J. J. DeFrank, J. R. Wild, "Enzyme-Based Biosensor for the Direct Detection of Fluorine-Containing Organophosphates," Anal. Chim. Acta 2001, 442, pp. 15-23.

Spichiger-Keller, U. E., "Ion- and Substrate-Selective Optode Membranes and Optical Detection Modes," Sens. Actuators 1997, B 38-39, pp. 68-77.

Steinle, E. D., U. Schaller, M. E. Meyerhoff, "Response Characteristics of Anion-Selective Polymer Membrane Electrodes Based on Gallium(III), Indium(III) and Thallium(III) Porphyrins," Anal. Sci. 1998, 14, pp. 79-84.

Steinle, E. D., S. Amemiya, P. Bühlmann, M. E. Meyerhoff, "Origin of Non-Nernstian Anion Response Slopes of Metralloporphyrin-Based Liquid/Polymer Membrane Electrodes," Anal. Chem. 2000, 72, pp. 5766-5773.

Suksai, C., T. Tuntulani, "Chromogenic Anion Sensors," Chem. Soc. Rev. 2003, 32, pp. 192-202.

Togashi, D. M., S. M. B. Costa, A. J. F. N. Sobral, A. M. d'A. R. Gonsalves, "Self-Aggregation of Lipophilic Porphyrins in Reverse Micelles of Aerosol OT," J. Phys. Chem. B 2004, 108, pp. 11344-11356.

Toth, K., G. Nagy, B. T. T. Lan, J. Jeney, S. J. Choquette, "Planar Waveguide Ion-Selective Sensors," Anal. Chim. Acta 1997, 353, 1-10.

U.S. Environmental Protection Agency, Current Drinking Water Standards, "List of Drinking Water Contaminants & MCLs," EPA 816-F-02-013. Washington, DC: U.S. Environmental Protection Agency, Office of Water, Jul. 2002 (14 pages).

Wagner-Jauregg, T., B. E. Hackley, Jr., T. A. Lies, O. O. Owens, R. Proper, "Model Reactions of Phosphorus-Containing Enzyme Inactivators. IV. The Catalytic Activity of Certain Metal Salts and Chelates in the Hydrolysis of Diisopropyl Fluorophosphate," J. Am. Chem. Soc. 1955, 77, 922-929.

Wang, E., M. E. Meyerhoff, V. C. Yang, "Optical Detection of Macromolecular Heparin via Selective Coextraction into Thin Polymeric Films," Anal. Chem. 1995, 67, pp. 522-527.

Wolfbeis, O. S., "Fiber-Optic Chemical Sensors and Biosensors," Anal. Chem. 2004, 76, pp. 3269-3284.

Xiao, K. P., P. Bühlmann, S. Nishizawa, S. Amemiya, Y. Umezawa, "A Chloride Ion-Selective Solvent Polymeric Membrane Electrode Based on a Hydrogen Bond Forming Ionophore," Anal. Chem. 1997, 69, pp. 1038-1044.

Yuan, R., Y.-Q. Chai, D. Liu, D. Gao, J.-Z. Li, R.-Q. Yu, "Schiff Base Complexes of Cobalt(II) as Neutral Carriers for Highly Selective Iodide Electrodes," Anal. Chem. 1993, 65, pp. 2572-2575.

Zhan, C.-G., D. A. Dixon, "Hydration of the Fluoride Anion: Structures and Absolute Hydration Free Energy from First-Principles Electronic Structure Calculations," J. Phys.Chem. A 2004, 108, pp. 2020-2029.

Zhang, W., E. Rozniecka, E. Malinowska, E., P. Parzuchowski, M. E. Meyerhoff, "Optical Chloride Sensor Based on Dimer-Monomer Equilibrium of Indium(III) Octaethylporphyrin in Polymeric Film," Anal. Chem. 2002, 74, pp. 4548-4557.

* cited by examiner

FILMS FOR DETECTING FLUORIDE

CROSS-REFERENCE TO RELATED APPLICATIONS

This application claims the benefit of provisional application Ser. No. 60/664,310, filed Mar. 22, 2005.

STATEMENT REGARDING FEDERALLY SPONSORED RESEARCH OR DEVELOPMENT

This invention was made in the course of research supported by a grant from the National Institutes of Health (NIH), Grant No. EB 000784. The U.S. government has certain rights in the invention.

BACKGROUND

The present disclosure relates generally to organic films, and more particularly to films for detecting fluoride.

Chemical sensors, including electrochemical (potentiometric ion-selective electrodes, conductometric sensors, and the like) and optical sensors, may be designed with selective response to given cations using various natural antibiotics (e.g., valinomycin), crown ethers, calixarenes and other ionophore-type structures within thin organic liquid or polymeric membranes/films. However, the design of analogous anion selective sensors has been far more difficult, due, at least in part, to the lack of suitable lipophilic host molecules that exhibit specificity for interaction with given anions. Further, organic membrane/film type sensors with selective response to fluoride, in particular, may be difficult to achieve because of the negative Gibbs free energy of hydration of this anion relative to others (−436 kJ/mol). Hence, achieving fluoride extraction into low dielectric constant organic liquid or polymeric films with selectivity over anions with much more positive free energies of hydration (e.g., perchlorate, −201 kJ/mol) may require an exceptionally high degree of anion binding discrimination by the host molecule to overcome the favorable single ion partition coefficients associated with such interferent anions.

A variety of metal-ligand complexes, for example, metalloporphyrins and related structures, have been examined as potential ionophores in organic membranes/films to prepare useful anion sensors using both optical and potentiometric modes of detection. Selectivity is achieved based on the relative binding interactions of anions as axial ligands with the metal ion-ligand complexes within the organic films. Films doped with gallium(III) and zirconium(IV) porphyrins display enhanced selectivity for fluoride ions, although, in some instances, the sensitivity is not adequate for certain applications (e.g., detecting fluoride levels in municipal drinking waters). Further, the selectivity over other anions (e.g. thiocyanate, perchlorate, salicylate, and iodide) may be marginal for practical applications.

As such, it would be desirable to provide a film and sensor having relatively high selectivity for fluoride ions.

SUMMARY

A film for detecting fluoride is disclosed herein. The film includes an organic matrix having a lipophilic aluminum compound incorporated therein. The lipophilic aluminum compound is adapted to selectively bind with fluoride ions. The fluoride is detectable through optical or electrochemical detection of the binding interaction. The film may be incorporated into an optical sensor and/or an electrochemical sensor configuration for the selective determination of fluoride in a wide range of samples.

BRIEF DESCRIPTION OF THE DRAWINGS

Objects, features and advantages of embodiments of the present disclosure will become apparent by reference to the following detailed description and drawings, in which.

DETAILED DESCRIPTION

It is known that aluminum ions in aqueous solution are capable of binding to fluoride ions and forming highly stable complexes. For example, in solution phase chemistry, fluoride is usually used as a masking agent for aluminum ions, which indicates a high affinity of aluminum ion toward fluoride ions compared to the affinity of other cations towards fluoride ion. However, aluminum-fluoride binding capability in aqueous solution is not necessarily indicative of the selective binding capability of various aluminum containing compounds or their ability to bind fluoride when incorporated into an organic membrane/film. As such, lipophilic aluminum compounds have not been utilized to date in the development of analytical methods/devices for the measurement of fluoride ion(s). Generally speaking, the selectivity of metal ion complexes is dictated, at least in part, by the nature of the metal ion center. More specifically, comparative binding, that is, the relative binding affinity of different ions to the metal ion of a metal-ligand complex is an important factor that dictates the analytical selectivity of any device that incorporates aluminum ion-complexed species within an organic membrane/film. The present inventors have unexpectedly and fortuitously discovered that aluminum compounds bind fluoride ions with unexpectedly high selectivity, and this enables the accurate measurement of fluoride concentrations optically or electrochemically. Embodiment(s) of the films and sensors described herein advantageously incorporate an aluminum compound in an organic matrix. It is believed that the aluminum compound is capable of selectively (over other anions) extracting the fluoride ions (which are highly hydrophilic and much prefer the aqueous phase) into the organic phase, due at least in part to the surprisingly high fluoride selective binding affinity to the aluminum metal ion center within the aluminum compound.

Some embodiment(s) of the film and sensor described herein also employ the principles of anion/proton co-extraction chemistry to achieve optical responses. Without being bound to any theory, it is believed that the selectivity achieved with embodiment(s) of the film and sensor may be greater than that achieved for a solid-state fluoride selective membrane electrode that is based on a single crystal of lanthanum fluoride ($LaF_3$). An embodiment of the sensor incorporates an aluminum(III) porphyrin doped film, which provides a relatively inexpensive optical or electrochemical sensor with the capability of improved analytical performance for fluoride detection.

Figure 1A:
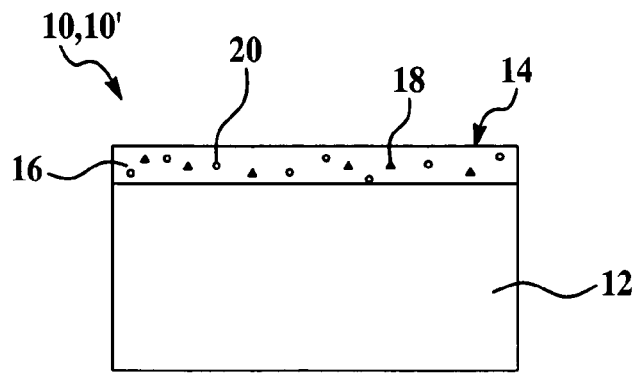
FIG. 1A is a schematic view of an embodiment of a film established on a substrate.
Figure 1B:
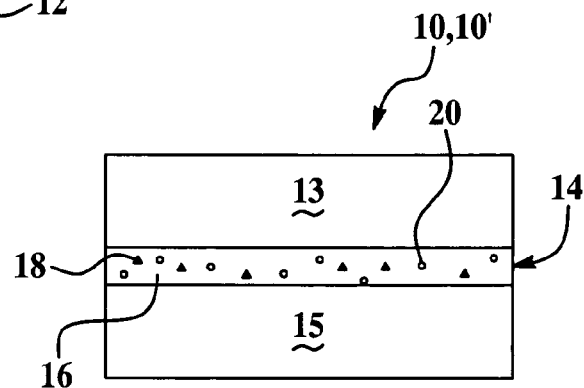
FIG. 1B is a schematic view of an embodiment of a film established between two solutions.

Referring now to FIGS. 1A and 1B, embodiments of two sensors 10 are depicted. As depicted in FIG. 1A, one embodiment of the sensor 10 includes a film 14 established on a substrate 12. As depicted in FIG. 1B, another embodiment of the sensor 10 includes a film 14 established between two aqueous phases 13, 15.

It is to be understood that in an embodiment where the film 14 is established on a substrate 12, any suitable substrate 12 may be selected. Non-limitative examples of the substrate 12 includes quartz slides/plates, glass slides/plates, distal ends of optical fibers, microfabricated sensor arrays, microfluidic platforms, and/or the like, and/or combinations thereof.

Further, it is to be understood that any suitable method may be employed to establish the film 14 on the substrate 12. In an embodiment, the film 14 components are dissolved in a solvent (e.g. tetrahydrofuran) and are cast on the substrate 12. Some suitable casting techniques include, but are not limited to spin coating, dip coating, screen printing, and/or combinations thereof. It is to be understood that the thickness of established film 14 may be any thickness suitable for a particular application. In an embodiment for substantially fully reversible optical sensors, the thickness of the established film 14 on the substrate 12 may range from about 0.1 μm to about 5 μm; in an alternate embodiment, the thickness of the established film 14 on the substrate 12 may range from about 5 μm to about 10 μm.

Further, it is to be understood that the film 14 may be thicker for electrochemical sensors and/or for single use optical sensors. In an embodiment, the film 14 thickness may be up to about 1 mm. In another embodiment, the film thickness may range from about 200 μm to about 500 μm. It is to be yet further understood that the film 14 may be established on a solid-state electrochemical sensor, where the film 14 has a thickness of about 50 μm.

The embodiment of the sensor 10 shown in FIG. 1B includes the film 14 in an ion-selective membrane electrode configuration. In this embodiment, the film 14 separates two aqueous phases. In a non-limitative example, the film 14 separates a sample phase 13 from an internal reference solution phase 15.

The film 14 includes an organic matrix 16 doped with a lipophilic aluminum compound 18. The organic matrix 16 may include any suitable organic solvents (non-limitative examples of which include at least one of chloroform, toluene, or the like), polymers (non-limitative examples of which include at least one of poly(vinyl chloride), polyurethane, silicone rubbers, cellulose acetate, poly(vinyl chloride)—poly(vinyl acetate) copolymers, and the like), and/or the like. The organic matrix 16 may be a bulk solution/extraction phase. Further, the organic matrix 16 may also include a plasticizer, such as, for example, o-nitrophenyloctyl ether (o-NPOE) or dioctyl sebacate (DOS). It is to be understood that a plasticizer may be desirable when the organic matrix 16 is a polymeric film.

The lipophilic aluminum compound 18 incorporated within the organic matrix 16 may be lipophilic aluminum metal-ion complexes (non-limitative examples of which include aluminum salophens, aluminum salens, and aluminum phthalocyanines), lipophilic aluminum porphyrins, aluminum Schiff base complexes, and/or combinations thereof.

Figure 2:
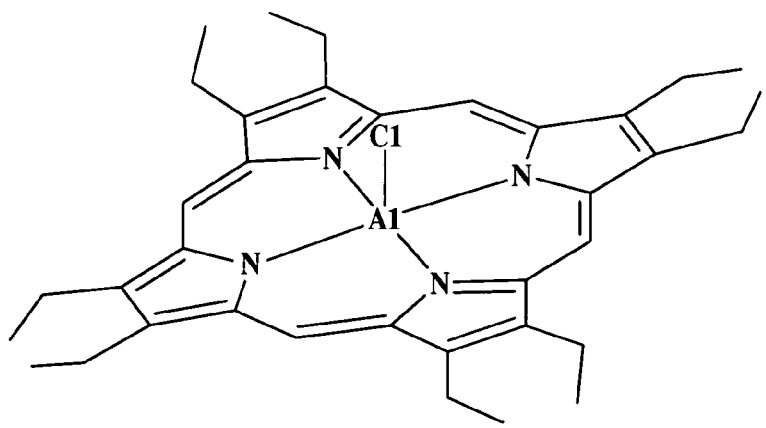
FIG. 2 is the chemical structure of chloro-aluminum(III) octaethylporphyrin (Al[OEP])
Figure 3:
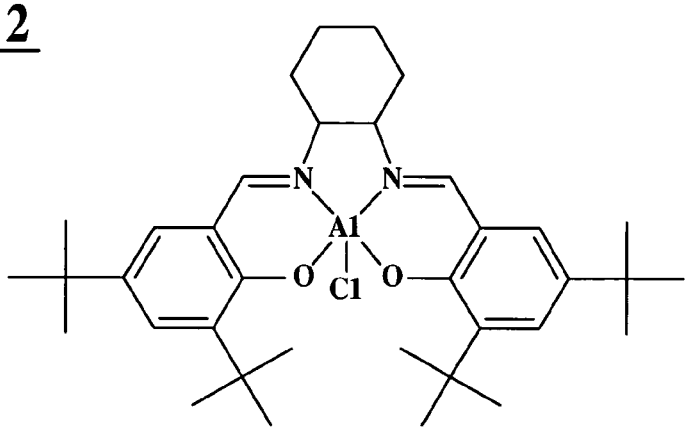
FIG. 3 is the chemical structure of chloro-aluminum(III) salen.
Figure 4:
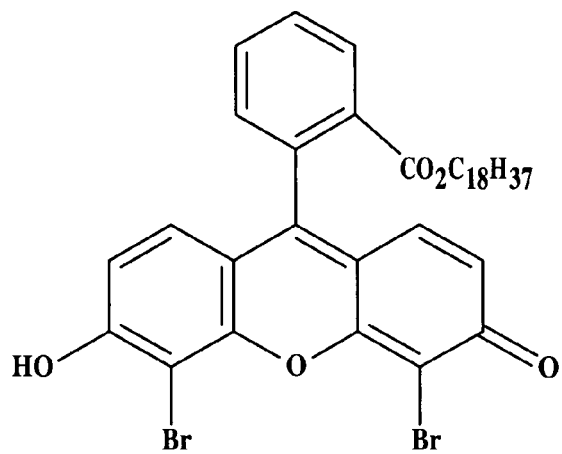
FIG. 4 is the chemical structure of 4',5'-dibromofluorescein octadecyl ester (ETH-7075)

A non-limitative example of a lipophilic aluminum porphyrin includes aluminum(III)octaethylporphyrins (Al[OEP]), the structure of which is depicted in FIG. 2. A non-limitative example of a lipophilic aluminum metal-ion complex is chloro-aluminum(III)salen (i.e. (R,R)-N,N'-bis(3,5-di-tert-butyl-salicylidene-1,2-cyclohexane diamino-aluminum(III) chloride ionophore or Al-Sal), the structure of which is depicted in FIG. 3. Other non-limitative examples of suitable lipophilic aluminum porphyrins include aluminum(III) tetraryl porphyrins (e.g., tetraphenyl (TPP) or substituted tetraphenyl porphyrins), aluminum(III)octaalkyl porphyrins (e.g., octadecyl or octadodecyl porphyrins), and sterically hindered Al(III)picket fence porphyrin (PFP) complexes (e.g., 5,10,15,20-tetrakis(o-pivalamidophenyl)porphyrin). It is to be understood that the lipophilic aluminum compound 18 is highly selective to fluoride ions. This may be due, at least in part, to the native binding interaction of the Al(III) center to selectively coordinate with fluoride over other anions.

Without being bound to any theory, it is believed that stability constant data reveals that the stability of aluminum (III) fluoride ion complexes is very high compared to that of other metal ion-fluoride complexes. Further, it is believed that the binding constant of fluoride ions with the aluminum(III) center of the porphyrin structure is high compared to that of other metal ion-fluoride complexes.

When the film 14 or sensor 10 incorporating film 14 is exposed to a sample containing fluoride ions, the fluoride ions selectively bind to the aluminum compound 18. Upon the interaction and binding of the fluoride ions with the aluminum compound 18 of the film, the concentration of fluoride may be detected optically or electrochemically.

In an embodiment, the binding may be transduced optically based on a change in the fluorescence, visual color, and/or absorbance (measured either by reflectance or transmission), and/or the like of the aluminum compound 18 within the film 14.

In an alternate embodiment, the fluoride concentration may be determined by monitoring a change in an electrochemical property of the film 14. The electrochemical properties may be monitored via voltammetry, amperometry, coulometry, potentiometry, conductivity, and/or the like, and/or combinations thereof.

For substantially fully reversible potentiometric devices, the membrane may already be equilibrated with fluoride ion(s), and there may be no further measurable extraction/binding of fluoride into the film. In such cases, the "potential" for such extraction and transport through the film is measured.

In one embodiment, the sensor 10 is capable of producing an optical signal originating from the porphyrin spectra in the case of sensors based on aluminum porphyrins, without the addition of a predetermined additive (described further hereinbelow). Without being bound to any theory, it is believed that this optical signal is produced by a dimer-monomer equilibrium. It is to be understood, however, that in some embodiments (e.g. those including a predetermined additive) the formation of dimers may not be desirable. In a non-limitative example embodiment, the sterically hindered Al(III)picket fence porphyrin complex generally does not undergo dimer-monomer equilibria reactions.

The embodiment of the sensor 10 without addition of a predetermined additive may be useful for single use devices, such as a disposable color strip test, which are generally not pre-equilibrated with fluoride. It is also to be understood that this embodiment may, in some instances, be adapted for use in a re-usable device.

In an alternate embodiment where the sensor 10 produces an optical signal, a predetermined additive 20 (as shown in FIG. 1) may be incorporated within the organic matrix 16 in addition to the aluminum compound 18. In an embodiment, the additive 20 transduces to an optical signal the binding interaction of the fluoride ions to the lipophilic aluminum compound 18. It is to be understood that the signal corresponds to the concentration of the fluoride ions binding to the aluminum compound 18.

In a non-limitative example, the additive 20 may be a lipophilic pH chromoionophore. A non-limitative example of a pH chromoionophore includes 4'5'-dibromofluorescein octadecyl ester (ETH-7075). Without being bound to any theory, it is believed that the addition of the pH chromoionophore to a film 14 used in an optical sensor 10 substantially enhances the reversibility of the system and substantially reduces the response time for the binding and dissociation of fluoride ions to the Al(III) species. Further, to maintain charge neutrality, a proton may be co-extracted to protonate the pH chromoionophore. Without being bound to any theory, it is believed that proton exchange occurs to maintain charge neutrality within the organic film 14, thereby yielding the optical response.

An additive 20 may also be incorporated into a sensor 10 that is capable of electrochemically detecting fluoride. In this embodiment, it is to be understood that the additive 20 may enhance the electrochemical performance of the sensor 10 by improving the selectivity or inducing enhanced anionic response. Non-limitative examples of such additives 20 include lipophilic anionic sites (non-limitative examples of which include tetraphenylborate derivatives); and/or lipophilic cationic sites (non-limitative examples of which include quaternary ammonium salts).

It is to be understood that the film 14 or sensor 10 (without the incorporation of an additive such as a chromoionophore) that is capable of producing an electrochemical signal may be used as an electrode 10' (see FIG. 1).

Figure 5:
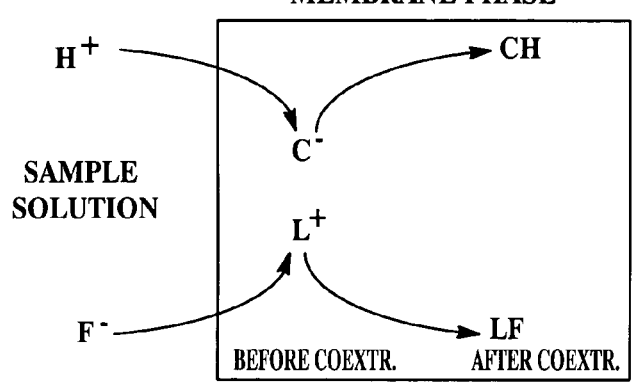
FIG. 5 is a graph depicting an optical sensing scheme for fluoride ions using a charged carrier L+ (Aluminum complex) coupled with a lipophilic acidic dye C− in the deprotonated form; and CH is the protonated form of the lipophilic dye.

Referring now to FIG. 5, an optical sensing scheme for fluoride ions is depicted. A charged carrier [L+] (e.g. Al[OEP]) is co-incorporated within the film with a lipophilic acidic dye. [C−] (e.g. ETH-7075) in the deprotonated form. [CH] represents the protonated form of the lipophilic dye.

Experimental

Optical Sensor with Film including a Predetermined Additive

A thin polymeric film (2 μm-5 μm; o-nitrophenyl octyl ether (o-NPOE) plasticized poly(vinyl chloride)) was doped with chloro aluminum(III)octaethylporphyrin (Al[OEP]) and a lipophilic pH indicator (ETH-7075; 4',5'-dibromofluorescein octadecyl ester).

The casting cocktail contained 72 mmol/kg Al[OEP], 33 wt % PVC, 66 wt % o-NPOE and 100 mol % (relative to fluoride ionophore) ETH-7075. The cocktail was cast on a quartz slide.

Figure 6:
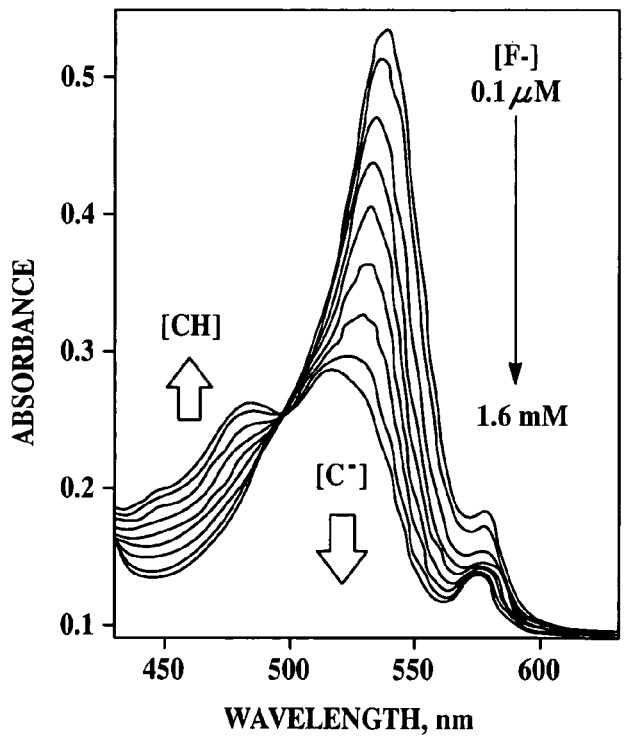
FIG. 6 is a graph depicting the spectral change of an Al[OEP]/ETH-7075 based fluoride optical sensor when exposed to different concentrations of fluoride ion.

The lipophilic pH chromoionophore transduced the binding event of the fluoride ion to the Al[OEP] in the form of an optical signal. As shown in FIG. 6, when a buffer (0.1 M β-alanine adjusted to pH 3.6 using phosphoric acid) without any fluoride is flowed over the film (using flow-through configuration), the deprotonated form of the indicator dye (C⁻) ($\lambda_{max}$=537 nm) was the predominant absorbance band observed in the wavelength range of 450-550 nm. As fluoride is added to the buffer, the deprotonated band decreases in intensity, and the protonated form (CH) increases in absorbance ($\lambda_{max}$=470 nm).

Figure 7:
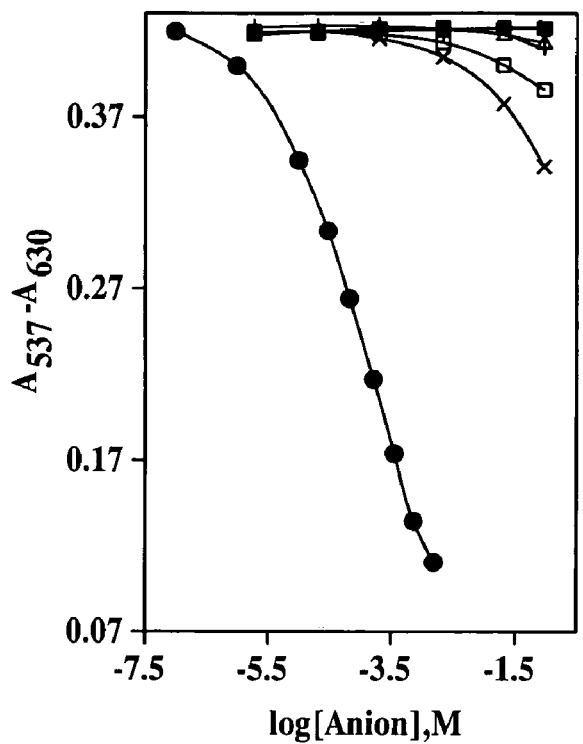
FIG. 7 is a graph depicting the absorbance response of an Al[OEP]/ETH-7075 based fluoride optical sensor toward different anions with the spectral change monitored at $\lambda_{max}$=537 nm vs. background absorbance at 630 nm.

FIG. 7, in general terms, illustrates a fluoride optical sensing film (based on Al[OEP] and a lipophilic pH-indicator) exhibiting a sub-micromolar detection limit and high discrimination for fluoride over several lipophilic anions such as nitrate, perchlorate and thiocyanate. More specifically, FIG. 7 shows the optical absorbance response of the Al[OEP]/ETH-7075 doped film at 537 nm toward changes in fluoride, as well as a host of other anions (fluoride (·), thiocyanate (×), perchlorate (□), nitrite (+), nitrate (Δ), chloride (■), bromide (■), and sulfate (■)) tested under the same conditions. Optical response toward fluoride was observed over the range of 0.1 μM-1.6 mM (or 1.9 ppb-30 ppm) total fluoride. As depicted, selectivity for fluoride over sulfate, chloride, nitrate, nitrite, bromide is relatively high (log $k^{opt}_{F,X}$<−5) and selectivity over highly lipophilic anions such as perchlorate and thiocyanate is also large (log $k^{opt}_{F,X}$≦−4). It is to be understood that the hydroxide ion may provide interference, and therefore a low pH buffer may be used to achieve low detection limits toward fluoride.

Figure 8:
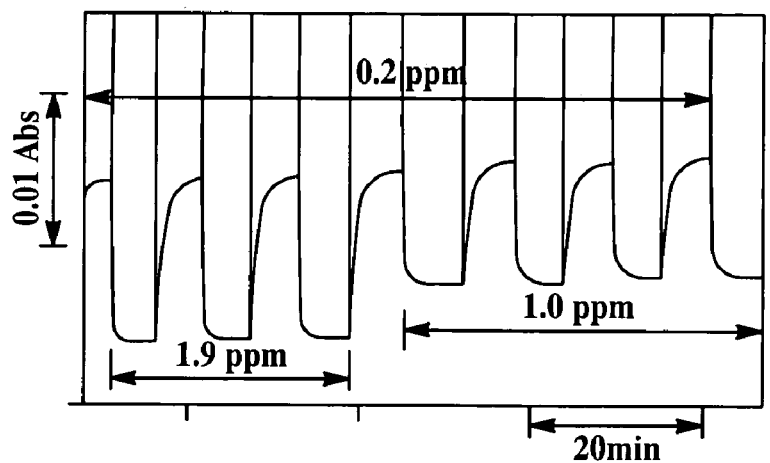
FIG. 8 is a graph depicting response and recovery time trace for an Al[OEP]/ETH-7075 based fluoride optical sensor measured when alternating flow solutions contain 0.2, 1.9, and 1.0 ppm total fluoride; absorbance monitored at 537 nm.

In the optical sensor having a film containing 16 mM/kg Al[OEP] and 100 mol % ETH-7075, the response to fluoride is advantageously reversible in the low concentration regime. FIG. 8 illustrates the absorbance signal for the deprotonated form of the chromoionophore within the film when solutions containing 0.2, 1.9, and 1.0 ppm total fluoride are alternately passed over the surface of the film in a flow-through sensing arrangement. Greater optical responses may be obtained if the films are employed as thin coatings on optical waveguides to obtain a longer effective pathlength for the absorbance measurements. The Al[OEP] based optical sensor is capable of detecting very low concentrations of fluoride ion in a substantially fully reversible and reproducible manner, which may advantageously be useful in many applications, including those having continuous or online monitoring of fluoride levels in, for example, water and/or other samples. The Al[OEP] based fluoride optical sensor is capable of detecting a relatively wide range of fluoride concentrations, such as for example, submicromolar concentrations up to millimolar concentrations.

Optical Sensor with Film without pH Chromoionophore Additive

Figure 9:
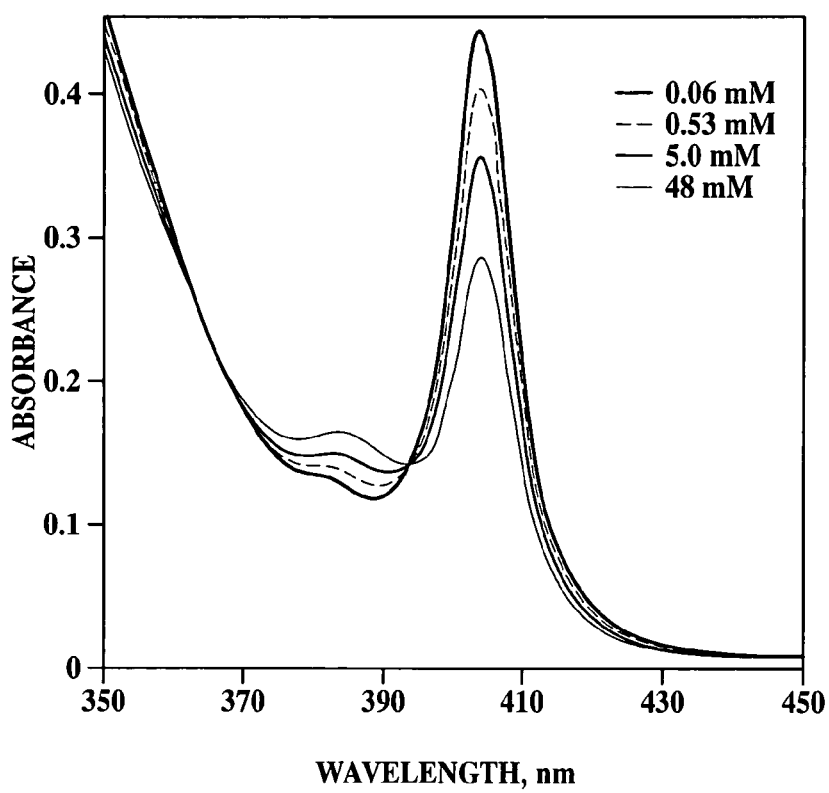
FIG. 9 is a graph depicting the optical absorbance response of Al(III)porphyrin based fluoride optical sensors toward varying fluoride concentration solutions.

The optical film was prepared using 1 wt. % Al(III)[OEP] and 100 mol % lipophilic borate in 33 wt. % PVC and 66 wt. % o-NPOE. This optical film did not include the lipophilic pH indicator. A large absorbance change in the Soret band (410-370 nm) occurred when the film was exposed to increasing fluoride concentrations (see FIG. 9). This film, or sensor incorporating this film, generally exhibited poor reversibility and therefore may be better suited as a single use fluoride measurement device/system.

Chloro-Al(III)Salen Electrochemical Sensor

Figure 10:
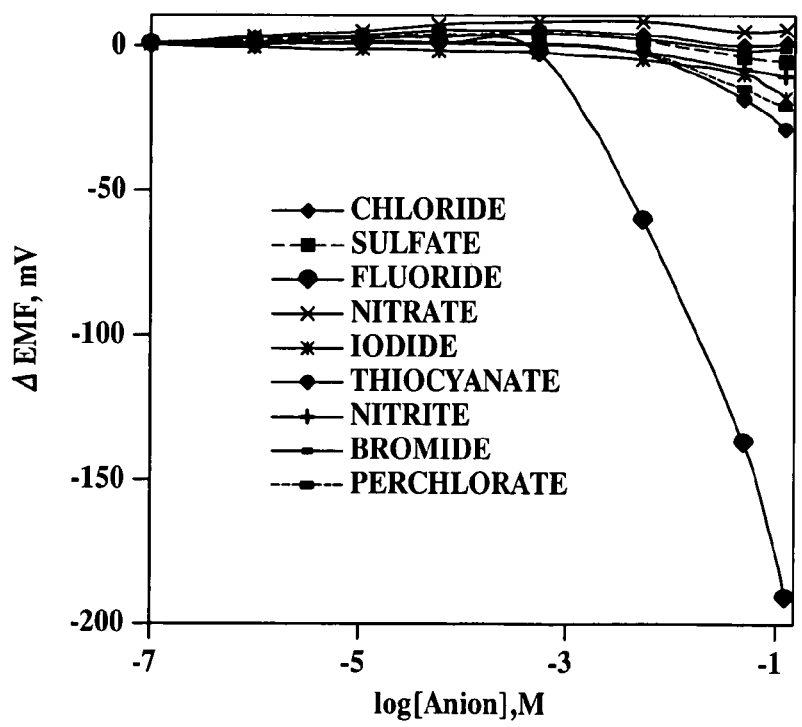
FIG. 10 is a graph depicting the potentiometric responses of an Al(III)Salen based fluoride sensor to various anions.

Polymeric ion-selective membrane electrodes were prepared using 33% PVC, 66% o-NPOE, 1 wt. % of chloro-Al (III)Salen, and 0.3 mol % borate additives. The fluoride response was measured in a test solution containing 0.05 M morpholinoethanesulfonic acid (MES), pH 5.0. The potentiometric anion responses of the electrochemical sensors are shown in FIG. 10. The electrodes show a large response to fluoride anions and minimal response to other anions. It is to be understood that a lower pH may be used to obtain an even better detection limit than that exhibited in FIG. 10.

Al[OEP], Al[TPP] and Al[PFP] Electrochemical Sensors

The membranes consisted of 1 wt. % of the selected ionophore, various quantities of anionic salt additives, and potassium tetrakis[3,5-bis(trifluoromethyl)phenyl]borate (KT-FPB) in about 66 wt. % plasticizer (o-nitrophenyloctyl ether (o-NPOE) or dioctylsebacate (DOS)) and about 33 wt. % polymer (poly(vinyl chloride) (PVC)). Detailed compositions of the membrane formulations are shown in Table 1.

TABLE 1

| Electrode identity | Ionophore | Plasticizer | mo % Borate | Internal Solution | F⁻ Slope (mV/dec) |
|---|---|---|---|---|---|
| I | Al[TPP] | DOS | 0 | Cl | −123.9 |
| II | Al[TPP] | DOS | 25 | Cl | −164.5 |
| III | Al[TPP] | DOS | 50 | Cl | −162.9 |
| IV | Al[TPP] | DOS | 75 | Cl | −169.8 |
| V | Al[TPP] | DOS | 100 | Cl | −35.1 |
| VI | Al[TPP] | DOS | 0 | Cl/F | −67.3 |
| VII | Al[TPP] | DOS | 25 | Cl/F | −56.1 |
| VIII | Al[TPP] | DOS | 50 | Cl/F | −55.0 |
| IX | Al[TPP] | DOS | 75 | Cl/F | −46.6 |
| X | Al[OEP] | DOS | 0 | Cl/F | −64.6 |
| XI | Al[OEP] | DOS | 25 | Cl/F | −54.5 |
| XII | Al[OEP] | DOS | 50 | Cl/F | −45.1 |
| XIII | Al[OEP] | DOS | 75 | Cl/F | −19.8 |
| XIV | Al[PFP] | NPOE | 0 | Cl | −55.3 |
| XV | Al[PFP] | NPOE | 25 | Cl | −59.4 |
| XVI | Al[PFP] | NPOE | 50 | Cl | −57.6 |
| XVII | Al[PFP] | DOS | 0 | Cl | −54.2 |
| XVIII | Al[PFP] | DOS | 25 | Cl | −55.0 |
| XIX | Al[PFP] | DOS | 50 | Cl | −50.2 |

The components (total mass=200 mg) were dissolved in 3-4 mL of distilled THF, and the mixture was cast in a 25 mm-id glass ring affixed to a glass slide. The solvent was allowed to evaporate overnight, and discs with 8 mm diameters were cut from the parent membrane and mounted in appropriate electrode bodies.

Electrochemical potentials were measured with the following galvanic cell: Ag/AgCl(s), KCl (4 M)/bridge electrolyte/ sample solution/ion-selective membrane/inner filling solution/AgCl(s)/Ag. The bridge electrolyte of the double junction reference electrode was 1 M lithium acetate. Buffered solutions of either 0.01 M NaCl or 0.01 M NaCl with 0.01 M NaF served as the inner filling and conditioning solution for the measurements. Buffers included 0.05 M 2-[N-morpholino]ethanesulfonic acid (MES) at pH 5.5, and 0.05 M glycine adjusted to pH 3.0 with phosphoric acid (gly/phos). All analyte solutions were prepared from sodium salts of the various anions dissolved in the appropriate buffer.

Potentiometric Response for Al[TPP] Membranes

Figure 11:
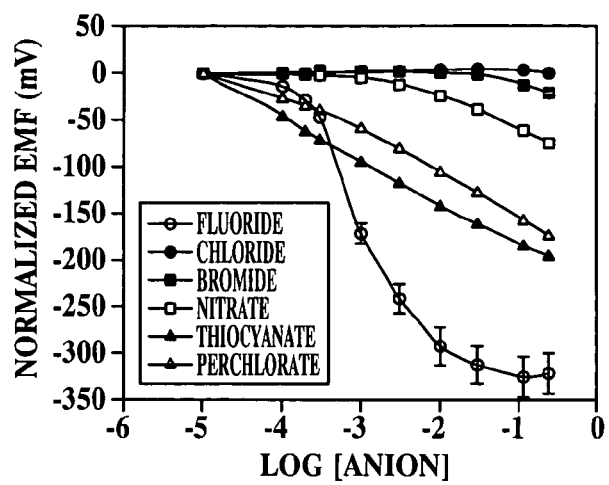
FIG. 11 is a graph depicting the potentiometric responses of an Al(III)-TPP based fluoride sensor to various anions.

FIG. 11 depicts the enhanced potentiometric response to fluoride compared to other anions of devices prepared with PVC-DOS membranes containing Al(III)-TPP (e.g., electrode III in Table 1).

Potentiometric Response for Al[PFP]

Figure 12:
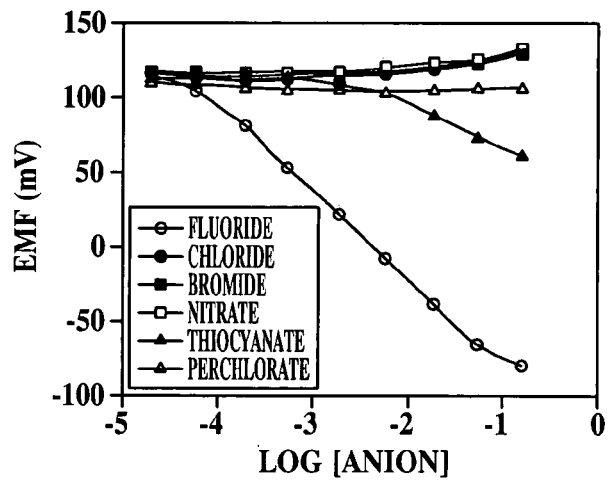
FIG. 12 is a graph depicting the potentiometric responses of an Al(III)-PFP based fluoride sensor to various anions.

Table 1 lists the membrane compositions that contained the Al(III)-PFP ionophore (electrodes XIV-XIX). FIG. 12 depicts the potentiometric response of electrode XV (PVC/ o-NPOE membrane containing 1 wt. % Al(III)-PFP and 25 mol % of KTFPB). When films of the same composition were examined using UV-Vis absorption spectroscopy, no evidence of any dimer formation was found in the absence or presence of fluoride, indicating that the steric hindrance within the PFP ligand substantially eliminates the possibility of forming anion bridged dimers. The changes in the spectrum (2 nm blue shift of the Soret band) reflected the axial ligation of fluoride to Al(III) ion center of the porphyrin.

Figure 13:
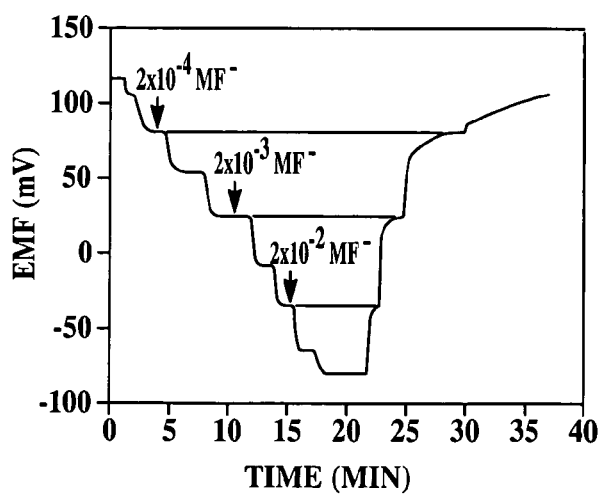
FIG. 13 is a graph depicting the potentiometric dynamic response and reversibility to fluoride of an Al(III)-PFP based fluoride sensor, where the horizontal lines represent equal concentrations.

FIG. 13 depicts the relatively rapid and fully reversible response of electrode XV toward fluoride. A response was achieved about 1 min after additions of fluoride to the test solution (pH 3.0) and full reversibility was achieved in about 2 to 3 minutes.

Comparative Data

Figure 14:
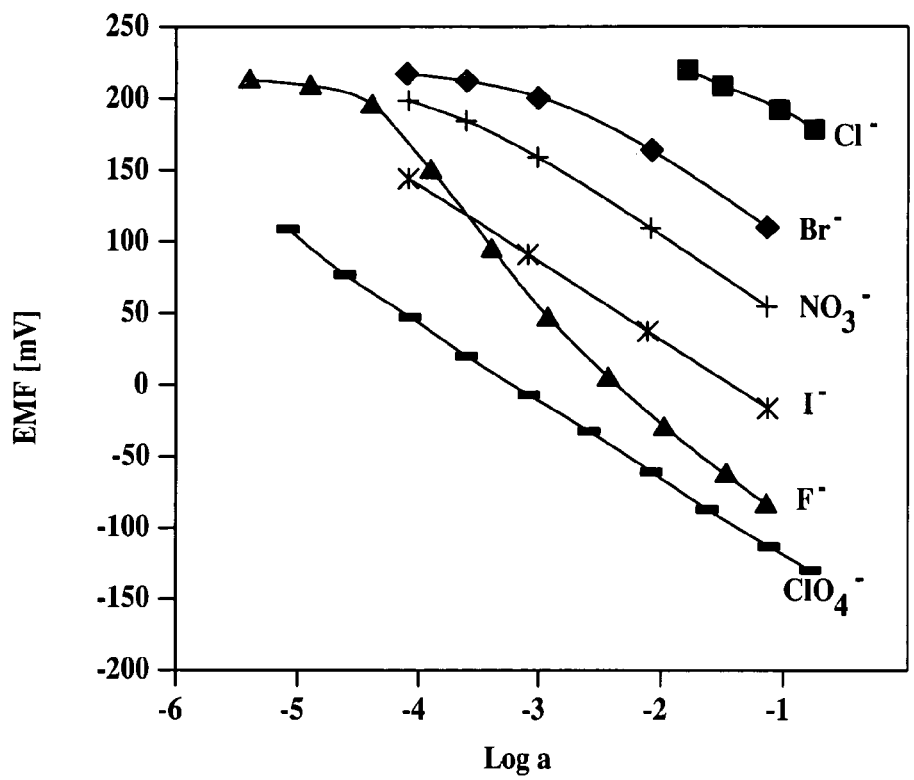
FIG. 14 is a graph depicting the potentiometric anion responses, measured in glycine-HCl buffer 3.0, for an optimized membrane electrode prepared with 1.0 wt. % chloro-zirconium(IV)octaethylporphyrin, PVC/o-NPOE (1:2), and 10 mol % (relative to the ionophore weight) lipophilic borate.
Figure 15:
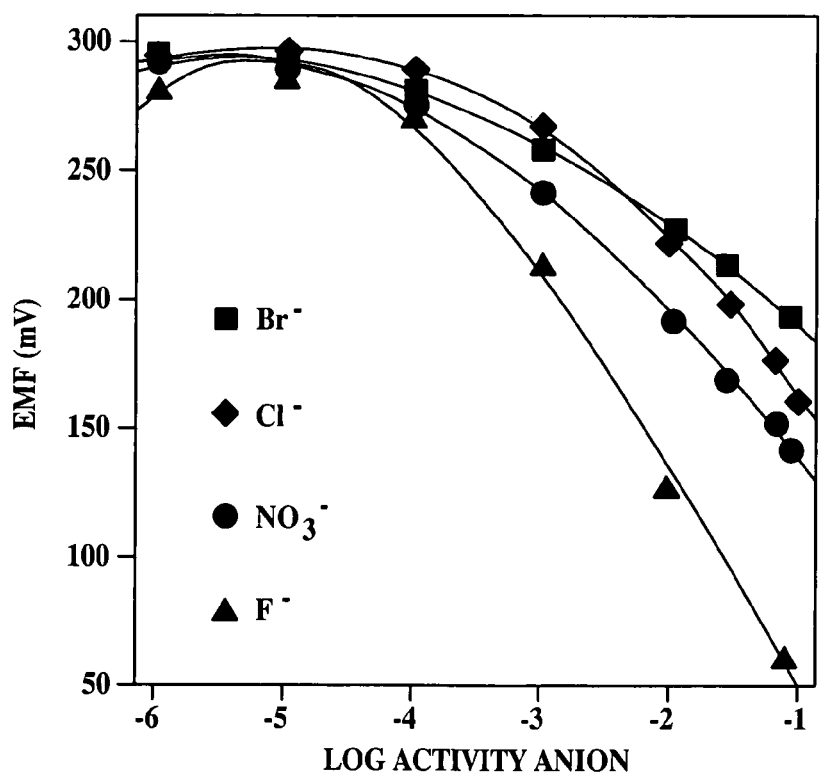
FIG. 15 is a graph depicting the potentiometric anion responses, measured in distilled deionized water, for optimized membrane electrodes prepared with 1.0 wt. % chloro-gallium(III)octaethylporphyrin, PCV/o-NPOE (1:2), and 21 mol % (relative to the ionophore weight) lipophilic borate.

FIGS. 14 and 15 respectively illustrate the potentiometric anion responses of a zirconium and a gallium porphyrin based electrochemical sensors. The anion selectivity patterns of the fluoride optical sensor based on Al(III)[OEP] as depicted in FIG. 7 and the anion selectivity patterns of the fluoride potentiometric sensor based on Al(III)[TPP] as depicted in FIG. 11 may be compared with the anion responses of a fluoride membrane electrode based on Zr(IV)[OEP] (FIG. 14) or the anion responses of a fluoride membrane electrode based on Ga(III)[OEP] (FIG. 15). A comparison with both FIGS. 7 and 11 indicates that the Al(III)[OEP] and the Al(III)[TPP] based sensors respond to fluoride with a much higher selectivity than either of the zirconium based and the gallium based sensors. As depicted, both the Al(III)[OEP] based optical sensor (FIG. 7) and the Al(III)[TPP] based electrochemical sensor (FIG. 11) detected minimal or no response from anions other than fluoride, while the Zr(IV)[OEP] and Ga(III)[OEP] responses suffer from interference of other lipophilic anions, such as perchlorate, bromide, iodide, and nitrate.

While the data reported in FIGS. 14 and 15 is electrochemical and not optical (as is the data reported in FIG. 7), the detected responses are useful for comparison purposes as they are based on the chemical interaction between the fluoride ions and the selected porphyrin centers. Indeed, the potentiometric and optical sensor selectivity patterns both originate from the relative binding affinities of the metal ion center of the lipophilic complex toward the target analyte anion (fluoride in this case) and the potential interferent anions.

Embodiment(s) of the film 14 and/or sensor 10 described herein may advantageously be designed as a single use system or may be designed as a reversible system. Further, the film 14 and/or sensor 10 incorporating the film 14 may be used in the determination of the fluoride levels in a variety of samples, including environmental samples (non-limitative examples of which include drinking, natural, and rain water), and industrial samples. The sensor 10 may be miniaturized as part of an optical fiber array designed for the analysis of gaseous or anionic species.

Embodiment(s) of the sensor 10 may also be used as indicator sensors for monitoring enzymatic reactions that produce or consume fluoride ions. For example, an Al(OEP) based fluoride sensor may be used to monitor glucose. This may be accomplished by monitoring the increase in fluoride ion concentration as a result of glucose oxidation catalyzed by glucose oxidase, which produces hydrogen peroxide, followed by monitoring an increase in fluoride ion concentration due to peroxidase catalyzed decomposition of fluoroaromatic compounds by the hydrogen peroxide produced from the glucose oxidase reaction. It is to be understood that the sensor 10 may be used in a similar manner for other oxidase substrates.

While several embodiments have been described in detail, it will be apparent to those skilled in the art that the disclosed embodiments may be modified. Therefore, the foregoing description is to be considered exemplary rather than limiting.

What is claimed is:

1. A film for detecting fluoride, the film comprising:
    an organic matrix; and
    a lipophilic aluminum compound including an aluminum metal ion center incorporated within the organic matrix, the lipophilic aluminum compound adapted to selectively bind with fluoride ions via a binding interaction between the aluminum metal ion center and the fluoride ions, the fluoride being detectable through optical or electrochemical detection of the binding interaction, the lipophilic aluminum compound selected from the group consisting of aluminum(III)octaethylporphyrins, chloro-aluminum(III)Salen, aluminum(III)tetraryl porphyrins, aluminum(III)octaalkyl porphyrins, and aluminum(III)picket fence porphyrins.

2. The film as defined in claim 1, further comprising an additive adapted to transduce an optical signal or enhance an electrochemical signal, the additive being incorporated within the organic matrix.

3. The film as defined in claim 2 wherein the fluoride is detectable through optical detection, and the additive comprises a lipophilic pH chromoionophore, the chromoionophore adapted to transduce to an optical signal the binding of fluoride to the aluminum compound.

4. The film as defined in claim 1 wherein the organic matrix is a polymeric matrix.

5. The film as defined in claim 1 wherein the organic matrix includes organic solvents, polymers, plasticizers, or combinations thereof.

6. The film as defined in claim 1 wherein the lipophilic aluminum compound is selected from the group consisting of chloro-aluminum(III)octaethylporphyrins, aluminum(III) tetraphenyl porphyrins, substituted aluminum(III)tetraphenyl porphyrins, aluminum(III)octadecyl porphyrins, aluminum(III)octadodecyl porphyrins, and aluminum(III)5,10,15, 20-tetrakis(o-pivalamidophenyl)porphyrin.

7. The film as defined in claim 1 wherein selectivity of the film, during optical detection, toward the fluoride ions over sulfate ions, chloride ions, nitrate ions, nitrite ions, and bromide ions is log $k^{opt}_{F,x} < -5$, and wherein selectivity of the film, during optical detection, toward the fluoride ions over lipophilic anions is log $k^{opt}_{F,x} < -4$.

8. The film as defined in claim 1 wherein ΔEMF in mV of the film during electrochemical detection of the fluoride ions has a more selective negative increase as compared to the sulfate ions, chloride ions, nitrate ions, nitrite ions, bromide ions, and lipophilic ions, as a log of the anion tends toward zero.

9. A film for optically detecting fluoride, the film comprising:
    an organic matrix;
    a lipophilic aluminum compound including an aluminum metal ion center incorporated within the organic matrix, the lipophilic aluminum compound adapted to selectively bind with fluoride ions via a binding interaction between the aluminum metal ion center and the fluoride ions, the lipophilic aluminum compound selected from the group consisting of aluminum(III)octaethylporphyrins, chloro-aluminum(III)Salen, aluminum(III)tetraryl porphyrins, aluminum(III)octaalkyl porphyrins, and aluminum(III)picket fence porphyrins; and
    a lipophilic pH chromoionophore incorporated within the organic matrix, the chromoionophore adapted to transduce the binding interaction to an optical signal.

10. The film as defined in claim 9 wherein the organic matrix is a polymeric matrix.

11. The film as defined in claim 9 wherein the organic matrix includes organic solvents, polymers, plasticizers, or combinations thereof.

12. The film as defined in claim 9 wherein the lipophilic aluminum compound is chloro-Al(III)Salen and wherein the film is a single-use film.

13. A method of making a sensor for optically detecting fluoride, the method comprising:
    incorporating a lipophilic aluminum compound including an aluminum metal ion center into an organic matrix, the lipophilic aluminum compound adapted to selectively bind with fluoride ions via a binding interaction between the aluminum metal ion center and the fluoride ions, and the fluoride being detectable through optical or electrochemical detection of the binding interaction, the lipophilic aluminum compound selected from the group consisting of aluminum(III)octaethylporphyrins, chloro-aluminum(III)Salen, aluminum(III)tetraryl porphyrins, aluminum(III)octaalkyl porphyrins, and aluminum(III)picket fence porphyrins; and
    dissolving the organic matrix having the aluminum compound therein in a solvent.

14. The method as defined in claim 13, further comprising establishing the solvent containing the dissolved organic matrix on a substrate.

15. The method as defined in claim 14 wherein the substrate is selected from the group consisting of quartz slides, quartz plates, glass slides, glass plates, distal ends of optical fibers, microfabricated sensor arrays, microfluidic platforms, and combinations thereof.

16. The method as defined in claim 13 wherein the organic matrix further includes an additive adapted to transduce an optical signal or enhance an electrochemical signal.

17. The method as defined in claim 16 wherein the fluoride is detectable through optical detection, and the additive comprises a lipophilic pH chromoionophore, the chromoionophore adapted to transduce to an optical signal the binding of fluoride to the aluminum compound.

18. The method as defined in claim 13, further comprising establishing the solvent containing the dissolved organic matrix between two aqueous phases.

19. A sensor for detecting fluoride, the sensor comprising:
an organic matrix; and
a lipophilic aluminum compound including an aluminum metal ion center incorporated within the organic matrix, thereby forming a film, the lipophilic aluminum compound adapted to selectively bind with fluoride ions via a binding interaction between the aluminum metal ion center and the fluoride ions, the fluoride being detectable through optical or electrochemical detection of the binding interaction, the lipophilic aluminum compound selected from the group consisting of aluminum(III) octaethylporphyrins, chloro-aluminum(III)Salen, aluminum(III)tetraryl porphyrins, aluminum(III)octaalkyl porphyrins, and aluminum(III)picket fence porphyrins; wherein the film is adapted to be established on a substrate or between two aqueous phases.

20. The sensor as defined in claim 19, further comprising an additive adapted to transduce an optical signal or enhance an electrochemical signal, the additive being incorporated within the organic matrix.

21. The sensor as defined in claim 20 wherein the fluoride is detectable through optical detection, and the additive comprises a lipophilic pH chromoionophore, the chromoionophore adapted to transduce to an optical signal the binding of fluoride to the aluminum compound.

22. The sensor as defined in claim 19 wherein the organic matrix is a polymeric matrix.

23. The sensor as defined in claim 19 wherein the organic matrix includes organic solvents, polymers, plasticizers, or combinations thereof.

24. The sensor as defined in claim 19 wherein the lipophilic aluminum compound is chloro-Al(III)Salen and wherein the sensor is a single-use device.

* * * * *